United States Patent [19]

Fleischer

[11] 4,241,861

[45] Dec. 30, 1980

[54] SCISSOR-TYPE SURGICAL STAPLER

[76] Inventor: Harry N. Fleischer, 700 Park Ave., New York, N.Y. 10022

[21] Appl. No.: 862,387

[22] Filed: Dec. 20, 1977

[51] Int. Cl.³ .............................................. B25C 5/02
[52] U.S. Cl. .................................... 227/135; 227/144; 227/153; 227/155; 227/DIG. 1
[58] Field of Search ................. 227/19, 135, 142, 143, 227/144, 152, 153, 155, DIG. 1

[56] References Cited

U.S. PATENT DOCUMENTS

| 1,446,107 | 2/1923 | Tibbals | 227/143 X |
|---|---|---|---|
| 2,813,269 | 11/1957 | Jacobs | 227/19 X |
| 3,022,510 | 2/1962 | O'Malley | 227/144 X |
| 3,269,631 | 8/1966 | Takaro | 227/19 X |
| 3,490,675 | 1/1970 | Green et al. | 227/19 |
| 3,646,801 | 3/1972 | Caroli | 227/19 X |

Primary Examiner—Paul A. Bell
Attorney, Agent, or Firm—Dressler, Goldsmith, Shore, Sutker & Milnamow, Ltd.

[57] ABSTRACT

A scissor-type surgical stapler is disclosed in which a pair of pivotally connected forcep handles are used with an elongated cartridge housing at the forward end of one of the handles, this cartridge housing being adapted to hold a staple cartridge containing a plurality of staples positioned in a line along the length of the housing, and an anvil is positioned in parallel apposition to the cartridge housing in line with the staples to be ejected from the staple cartridge, the anvil and the cartridge housing being interlinked so as to be relatively movable toward and away from each other while maintaining said parallel apposition as the handles are moved to open and close the staples.

2 Claims, 18 Drawing Figures

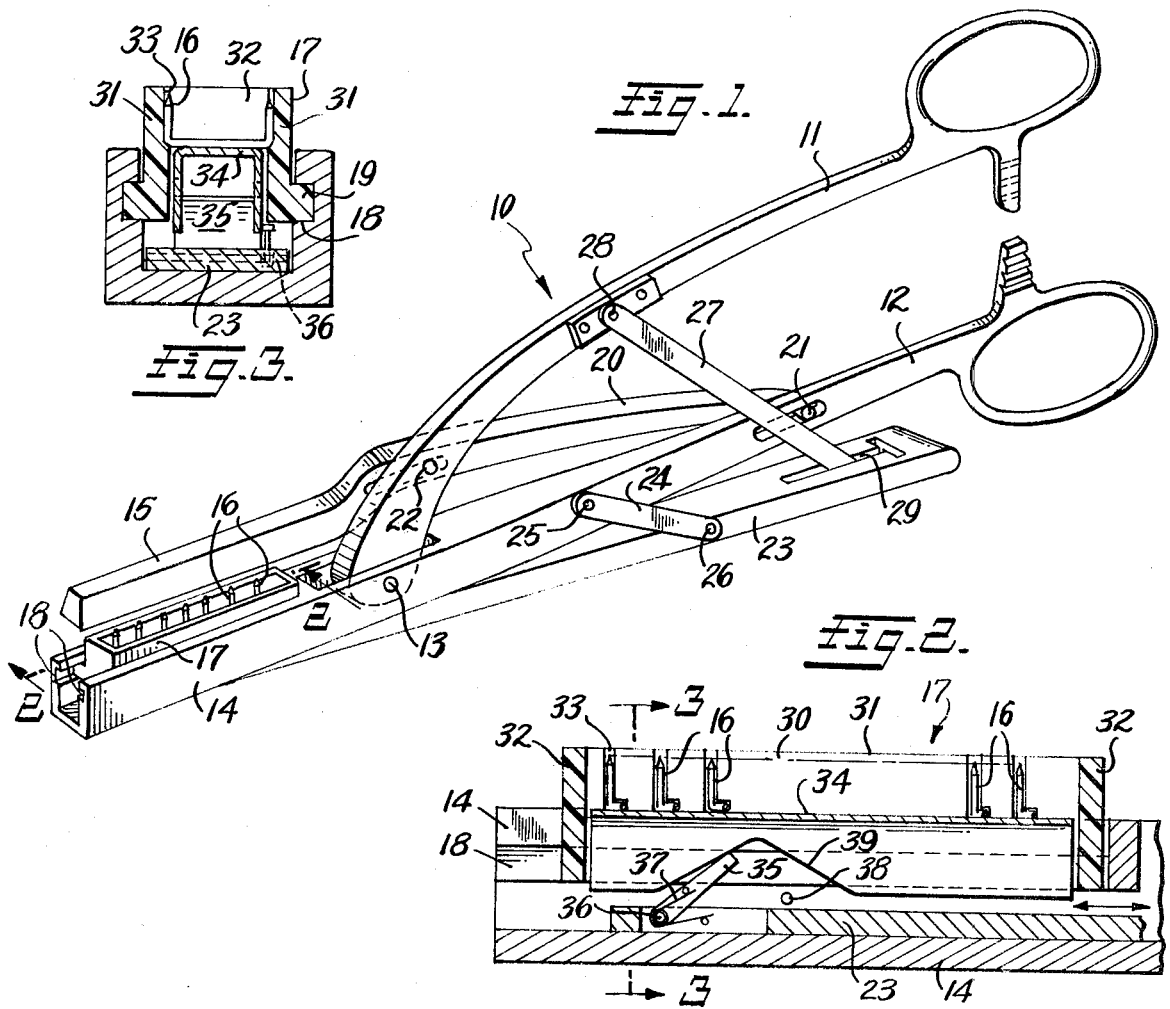

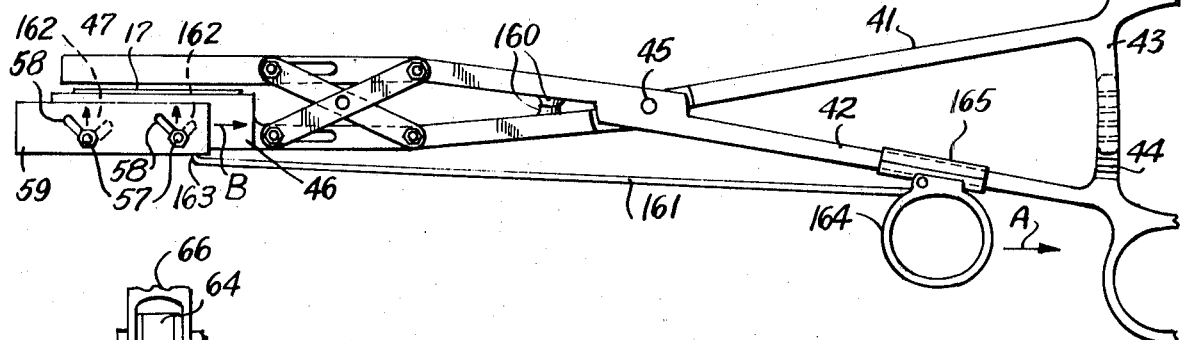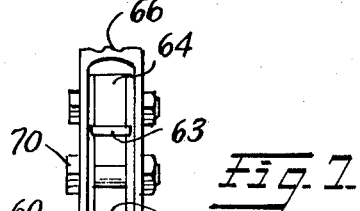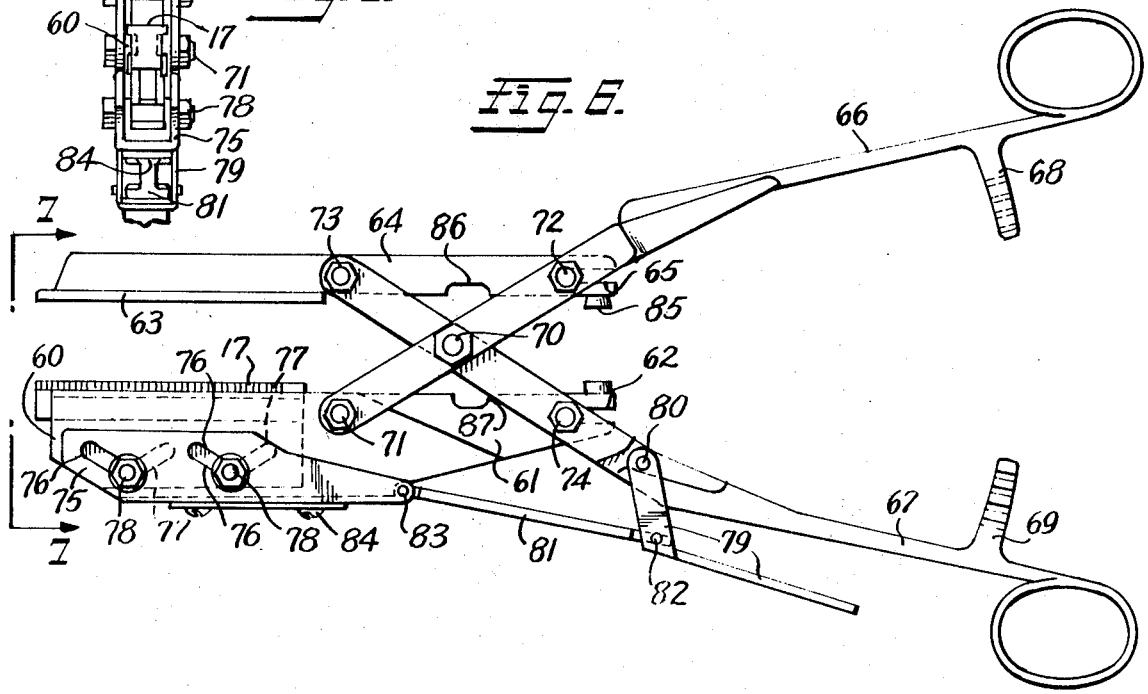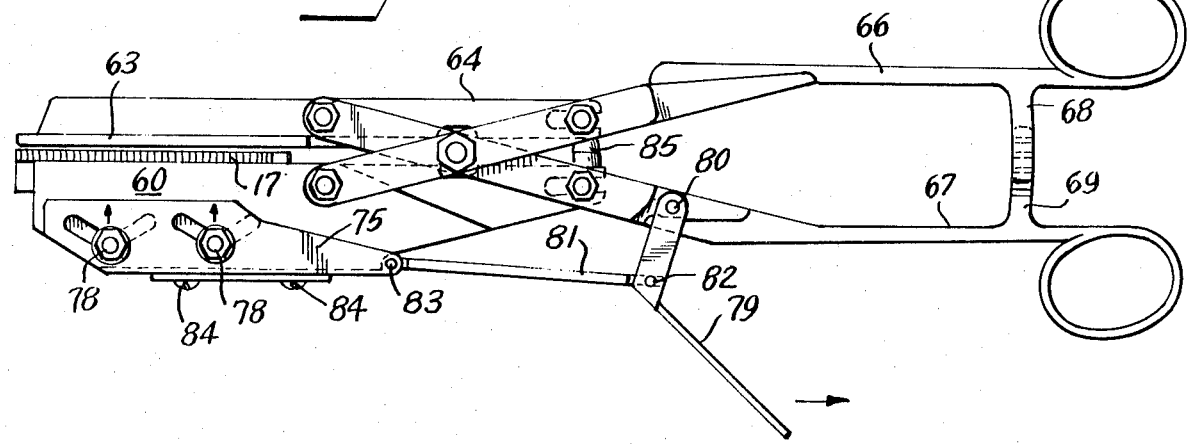

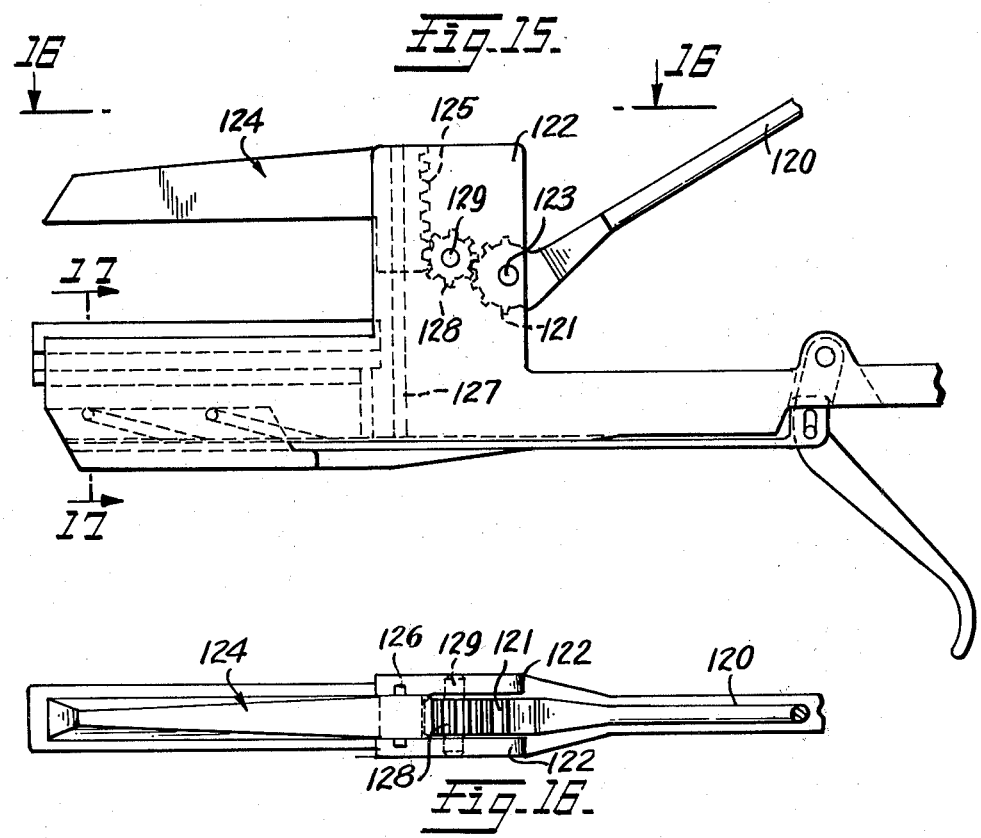
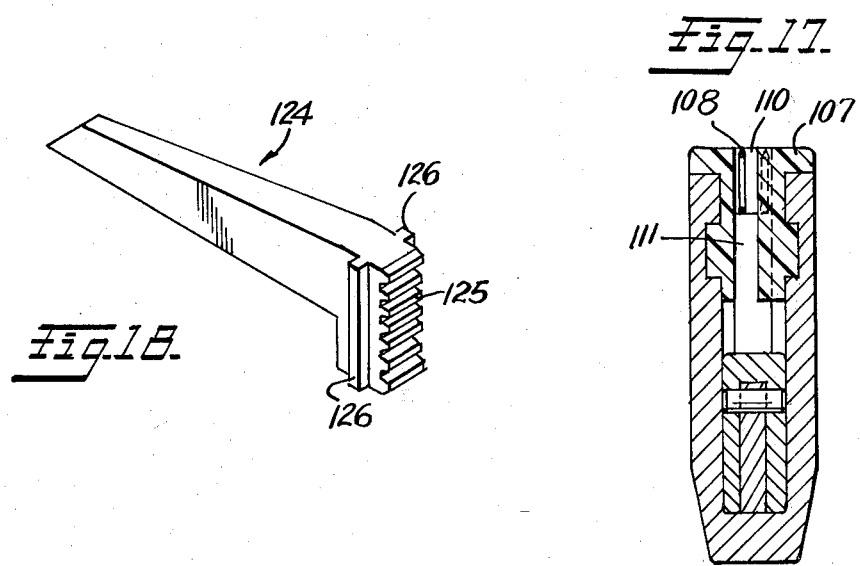

SCISSOR-TYPE SURGICAL STAPLER

The present invention relates to scissor-type surgical staplers.

Surgical staplers of wrench type are known, as illustrated in my prior U.S. Pat. No. 3,269,630, issued Aug. 30, 1966. However, a plier type stapler has many advantages over the wrench type stapler. More particularly, the wrench structure normally requires three operating steps. In the first step, the tissue or organ to be stapled is inserted between an anvil and a staple holder and a device is operated to bring these two elements together, as by rotating a screw mechanism, to clamp the tissue or organ between the operating elements of the stapler. The plier's handles are then operated to drive the staples home, whereupon the screw mechanism must be used again to separate the anvil and staple holder. These steps are slow and cumbersome, and while they are simplified to some extent in my said U.S. Pat. No. 3,269,630, the instrument is still clumsy to handle, and it is unlike the scissor-type instruments which surgeons are used to. Also, the lower abdomen is hard to reach with an instrument of conventional type.

Also, the prior instrument must be disassembled for sterilization, and then reassembled after each use, and this is difficult and time consuming.

Scissor-type surgical staplers have also been contemplated in Tokaro U.S. Pat. No. 3,269,631 issued Aug. 30, 1966, but here the staple housing and the mandrel associated therearenot maintained in parallel apposition as the handles are operated so that a plurality of staples aligned with the length of the instrument cannot be simultaneously applied as is normally desired.

This invention is directed to overcoming the inadequacies of the existing surgical staplers which apply staples in longitudinally extending rows. Features of especial importance are the scissor action, the achievement of one step or two step operation, ease of sterilization, and the capacity to employ staples which are at an angle to the line of suture.

In this invention, a scissor-type surgical stapler is provided in which a pair of pivotally connected forcep handles are movable from an open position to a closed position and an elongated cartridge housing adapted to support a staple cartridge containing a plurality of staples positioned in line with the length of the housing is provided at the forward end of one of the handles and an anvil is positioned in parallel apposition to the cartridge housing in line with the staples to be ejected from the staple cartridge. The anvil and the cartridge housing are interlinked so as to be relatively movable toward and away from each other while maintaining the parallel apposition as the handles are moved between the open and closed positions. Lastly, actuator means are associated with the cartridge housing to cause the ejection of staples from the staple cartridge when the handles are closed and means are provided to operate the actuator means when desired.

The invention and the several features thereof will be more fully apparent from the accompanying drawings in which:

FIG. 1 is a perspective view showing an illustrative structure in accordance with this invention;

FIG. 2 is a longitudinal cross-section of the cartridge housing of FIG. 1 showing the manner in which the actuator rod movement causes ejection of the staples;

FIG. 3 is a section taken on the line 3—3 of FIG. 2;

FIG. 4 is a side elevation of an alternative construction, the structure being shown open ready to receive tissue to be stapled;

FIG. 5 is another side elevation, the structure being shown in closed position ready for the operation of a separately manipulable actuator to cause staple ejection;

FIG. 6 is a side elevation of a preferred structure in accordance with the invention, the structure being shown in its open position;

FIG. 7 is an end view taken on the line 7—7 of FIG. 6;

FIG. 8 is another side elevation showing the structure of FIG. 6 in closed position ready for the operation of a lever-operated actuator;

FIG. 15 is a side elevation on still another construction in accordance with the invention;

FIG. 16 is a partial top plan view taken on the line 16—16 of FIG. 15;

FIG. 17 is a section taken on the line 17—17 of FIG. 15; and

FIG. 18 is a perspective view of the anvil-carrying jaw in FIG. 15.

Figure 9:
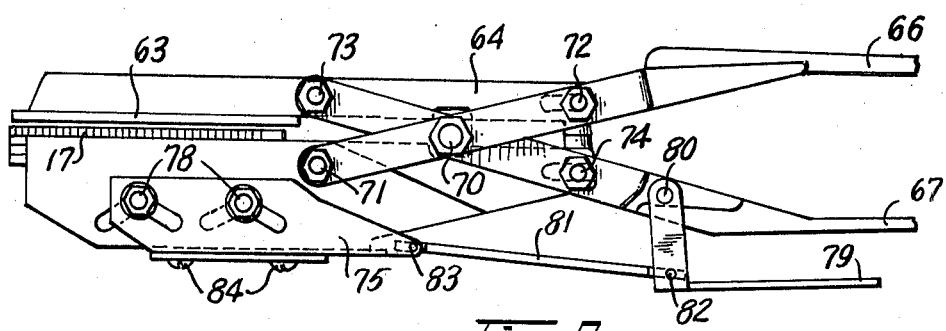
FIG. 9 is a side elevation like FIG. 8, but showing the operating lever after use.

Referring more particularly to FIG. 1, the surgical stapler 10 is formed by a pair of forcep handles 11 and 12 which are pivotally connected at 13. A cartridge housing 14 is formed at the forward end of the handle 12 and an anvil 15 which opposes the cartridge housing 14 is positioned in parallel apposition to the cartridge housing in line with the staples 16 which are ejected from a staple cartridge 17. As will be seen in FIG. 1, and especially in the cross-section of FIG. 3, the cartridge housing 14 is formed with longitudinal grooves 18 which slidingly receive the longitudinal ribs 19 on the sides of the staple cartridge 17.

The forcep handle 11 in the FIG. 1 construction is a compound handle, the forward end of it being provided by an arm 20 which is pivoted to the rear of handle 12 at 21 and to the midsection of handle 11 at 22. The anvil 15 is carried at the forward end of arm 20, and since handle 11 and arm 20 together constitute a composite handle, the anvil 15 is effectively at the forward end of handle 11.

As handles 11 and 12 are opened and closed, the cartridge housing 14 and the cartridge 17 therein are moved toward and away from the anvil 15, these two elements being maintained parallel to one another as they move, as is needed in order that a longitudinally extending row of staples might be applied. In this respect, the thickness of the tissue to be sutured can vary, but the distance between the anvil 15 and the cartridge 17 must be constant along the length of the cartridge.

When the cartridge 17 with the staples 16 within it is at the desired distance from anvil 15, staples are ejected to perform their stapling function. In the case of the FIG. 1 construction, staples ejection is a function of continued handle closure, but independent staple actuation is preferred.

The actuation of the staple ejector mechanism is provided by means of an actuator rod 23 which is slidingly mounted in the cartridge housing 14, see particularly FIGS. 2 and 3 where the forward end of actuator 23 is shown sliding at the bottom of the U-shaped cartridge housing 14. Returning to FIG. 1, actuator 23 is connected to handle 12 by link 24 and pivots 25 and 26 and the sliding movement of actuator 23 (see the double-ended arrow A in FIG. 2) is obtained by a pusher rod 27 which is pivoted at one end to the midsection of handle 11 at 28 with the other end sliding in a longitudinal channel 29 at the rear end of the actuator 23.

As a result of the above-described structure, when handles 11 and 12 are opened, the tissue or organ to be stapled can be inserted between the separated cartridge housing 14 and anvil 15. When the handles are closed, the cartridge 16 is brought to the proper distance from the anvil 15 whereupon further closing movement causes pusher 27 to force actuator 23 to the rear which causes staples 16 to be ejected as will now be described.

Referring to FIGS. 2 and 3, the staple cartridge 17, while it may be of conventional construction as illustrated in U.S. Pat. No. 3,490,675 issued Jan. 20, 1970, is preferably of special type in which the staples 16 are at an angle to the line of suture. In the structure shown, the staple cartridge 17 is constituted by a box-like body 30 having side walls 31 and end walls 32. The side walls 31 are grooved at 33 to receive the staples. The staples sit at the top of the box on top a staple driver 34 which is here constituted by an inverted U-shaped metal stamping which is frictionally held between the side walls 31. The side walls carry the ribs 19 which slide into the grooves 18 of the cartridge housing 14 which is of channel shape to receive the staple cartridge 17 and the actuator rod 23.

The forward end of actuator 23 carries a lifter 35 which is pivoted at 36 and biased upwardly by spring 37. As a result, when the staple cartridge 17 is slid into the open end of the channel-shaped cartridge housing 14, the driver 34 depresses lifter 35 to allow it to be fully inserted against stop 38. When actuator 23 is moved to the rear, lifter 35 overlies pin 38 which extends across the channel, so lifter 35 cannot be depressed and it functions to bear against cam surface 39 on the staple driver 34 to lift the driver and eject the staples 16. While only one lifter is shown in FIG. 2, more than one can be used.

An alternative construction is shown in FIGS. 4 and 5 where 41 and 42 identify the forcep handles which are formed with ratchets 43 and 44 which serve to lock the structure in its closed position. These handles are pivoted at 45 with handle 41 carrying cartridge housing 46 at its forward end and handle 42 carrying anvil 47 at its forward end. The anvil 47 and the cartridge 46 are maintained in parallel apposition by means of links 48 and 49 which are pivotally interconnected at 50. Link 48 is pivoted to handle 42 at 51, and it is slidably connected to handle 41 by pin 52 which slides in slot 53. Similarly, link 49 is pivoted to handle 41 at 54, and it is slidably connected to handle 42 by pin 55 which slides in slot 56.

Cartridge housing 46 carries a cartridge 17 as shown in FIGS. 2 and 3, and the lifters therefore are provided by lifting rods 57 which extend through the bottom of the channel shaped housing 46. These rods 57 are held in angled slots 58 in a U-shaped actuator 59 which surrounds the housing 46.

FIG. 5 shows the structure in its closed position, abutments 160 being shown for limiting the closing action. These abutments can be made adjustable so when the ratchets 43 and 44 are locked, the distance between the cartridge 17 and the anvil 47 can be predetermined. In this closed position, it will be seen that an actuator rod 161 is available and it can be pulled to the rear as shown by arrow A which serves to move actuator 59 to the rear as shown by arrow B. It will also be seen that rods 57 extend through housing 46 via slots 162 which extend at an angle to slots 58, so when actuator 59 is moved to the rear, lifting rods 57 are elevated to drive the staples home. Rod 161 is hooked to actuator 59 at 163 and it is secured at its other end to a finger loop 164 which slides on handle 42 by means of tube 165.

An important feature of the invention which is employed in preferred practice is the use of lifting rods which extend across the channel shaped housing 46 and which are elevated by an actuator which moves at an angle to the movement of the rods. Thus, the several staples sit atop a lifter which ejects them all simultaneously when rods 57 are elevated by the rearward movement of actuator 59. The structural simplicity which is here presented can be appreciated by comparing it with the construction shown in FIGS. 2 and 3.

The presently preferred form of the invention is shown in FIGS. 6 through 11 where it will be seen that the cartridge housing and the anvil are carried at the ends of arms which are pivotally connected to the pivotally interconnected handles, the handles serving as links. More particularly, a U-shaped cartridge housing 60 is carried at the forward end of cartridge arm 61 which is formed at the rear with a slot 62. Similarly, anvil 63 is carried at the forward end of an anvil arm 64 which is also slotted at the rear as indicated at 65. Handles 66 and 67 which carry interlinking ratchets 68 and 69 are pivoted to one another at 70. Handle 66 is pivoted to cartridge arm 61 at 71 and a sliding pivot is established with anvil arm 64 via pin 72 and slot 65. Similarly, handle 67 is pivoted to anvil arm 64 at 73 and a sliding pivot is estblished with cartridge arm 61 via pin 74 and slot 62.

The cartridge housing 60 is embraced within a U-shaped actuator 75 and the actuator 75 and the housing 60 are formed with two pairs of crossing slots 76 and 77 through which extend lifting rods 78. Actuator 75 is pulled rearwardly to operate the staple ejection operation by means of a lever 79 which is pivotally connected to handle 67 via pin 80 and to the connecting arm 81 via pivot 82. The connecting arm 81 pivotally joins actuator 75 at 83. Lastly, the bottom of actuator 75 and the bottom of the housing 60 are longitudinally slotted and held together by means of sliding bolts 84.

A threaded stop 85 adjustably limits closure of the handles 66 and 67, and recesses 86 and 87 receive the pin of pivot 70 in the closed position.

Operation of the device is simple. Handles 66 and 67 are separated as shown in FIG. 6, and the tissue to be stapled is inserted between the cartridge 17 held in cartridge housing 60 and the anvil 63. Handles 66 and 67 are then closed and, if desired, locked in their closed position by ratchets 68 and 69. Stop 85 adjustably limits the space between the anvil 63 and the staples when the structure is in the closed position shown in FIG. 8. After determining that the tissue has been properly grasped and is ready for stapling, the surgeon pulls level 79 rearwardly as shown by the arrow, and this pulls actuator 75 to the rear, forcing rods 78 upwardly which pushes the driver component of the staple cartridge 17 to cause the staples to be ejected and clenched against the anvil 63.

The actuation of the staples is best seen in FIG. 9 where lever 79 has been pivoted to slide actuator 75 to the rear which elevated lifting rods 78 to cause the staples to be rejected from cartridge 17 and clenched against anvil 63.

Figure 10:
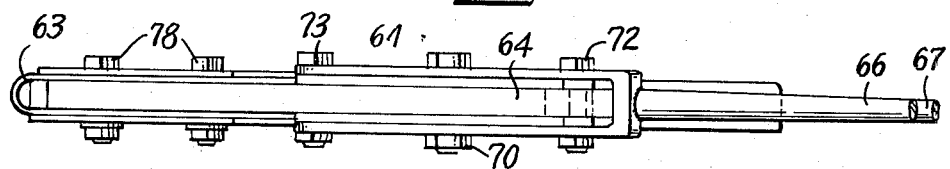
FIG. 10 is a top plan view of the structure shown in FIG. 9.
Figure 11:
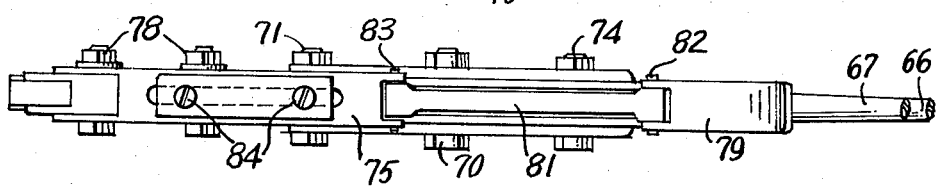
FIG. 11 is a bottom view of the FIG. 9 structure.

The top and bottom plan views of FIGS. 10 and 11 will serve to show details of construction.

Figure 12:
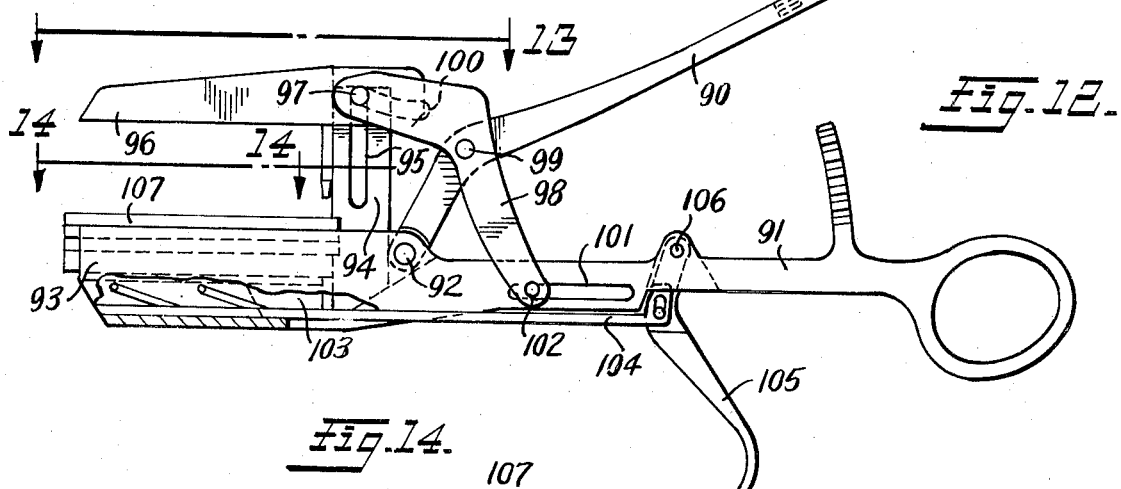
FIG. 12 is a side elevation of another construction in accordance with the invention.

Another construction is shown in FIG. 12 which employs an anvil which is slidingly mounted. Here, handles 90 and 91 are pivoted at 92 with the cartridge housing 93 being disposed at the forward end of handle 91. Handle 91 also carries a support 94 which is vertically slotted at 95 and anvil 96 is mounted via pin 97 for vertical sliding movement on the support 94. A link 98 is used to raise and lower anvil 96. The link 98 is pivoted to the handle 90 at 99, and it is slotted at 100 to receive pin 97. At the other end, link 98 slides in a slot 101 in handle 91 via pin 102.

The actuator for the staples is similar to that shown in FIG. 9, actuator 103 being pulled rearwardly by rod 104 when lever 105 is pivoted with respect to handle 91 around pivot 106. The top plan view of FIG. 13 will again help one to see the details of construction and FIG. 14 shows the staple cartridge 107 which is of different construction.

Figure 14:
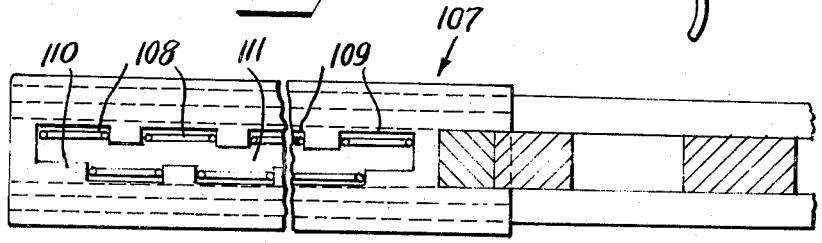
FIG. 14 shows a cartridge ejecting structure useful in the invention, this figure being a plan view on the line 14—14 of FIG. 12.

The cartridge 107 in FIG. 14 utilizes two rows of staples 108, each staple being positioned within its own recess 109 in a central vertical opening 110. The staples are ejected by the elevation of a driver 111 which fits within the opening 110 and underlies the staples.

Figure 13:
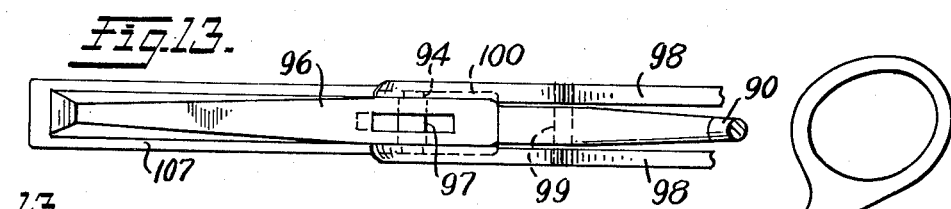
FIG. 13 is a partial top plan view taken on the line 13—13 of FIG. 12.

FIG. 15 shows a structure similar to the one shown in FIGS. 12 and 13, except that the handle 90 is replaced by a handle 120 which is formed with gear teeth 121 at its forward end and pivoted to the support 122 at 123. The rear of the anvil 124 pictured in FIG. 18 is formed with a rack 125 and is slidingly mounted on support 122 via ribs 126 which slide in grooves 127. Movement of handle 120 is transmitted to anvil 124 via intermediate gear 128 mounted on pin 129. Details of construction will again be evident from the plan view of FIG. 16.

FIG. 17 supplements the previous FIG. 14 since it is a vertical section from which it will be seen that cartridge 107 has a vertical opening 110 which carries staples 108 which sit on top of a driver 111 which fits within opening 110.

It will be understood that the lifting element in FIG. 17 which is the driver 111 can be formed with a central knife which extends upwardly between the two rows of staples, and the anvil can be formed with a central recess to receive the knife whereby the tissue can be severed between the rows of staples. Moreover, the cartridge can be made more complex to provide two rows of staples on each side of the cartridge. This provides an instrument for lateral gastrointestinal anastomosis which is the purpose of the instrument shown in U.S. Pat. No. 3,490,675 to D. T. Green.

The invention is defined in the claims which follow.

I claim:

1. A surgical stapler comprising an elongated cartridge housing of channel cross-section, said cartridge housing being adapted to hold at the open upper end of said channel a staple cartridge containing a plurality of staples positioned in a line along the length of the cartridge housing, said staple cartridge having the staples thereof positioned at the upper portion of the cartridge overlying a lifter which, when lifted, will cause the ejection of all of the staples, movable lifting rods extending across the lower portion of the channel of said cartridge housing, and means movable at an angle to the movement of said rods to cause said rods to be elevated to lift said lifter.

2. A scissor-type surgical stapler comprising a pair of pivotally connected forcep handles movable from an open position to a closed position, an elongated cartridge housing of channel shape at the forward end of one of said forcep handles, said cartridge housing being adapted to hold a staple cartridge containing a plurality of staples positioned in a line along the length of the cartridge housing, actuator means associated with said cartridge housing for operating said staple cartridge to cause the ejection of staples therefrom, said actuator means being constituted by a U-shaped member embracing the exterior of said cartridge housing, an anvil positioned in parallel apposition to said cartridge housing in line with the staples to be ejected from said staple cartridge, said anvil and said cartridge housing being interlinked so as to be relatively movable toward and away from each other while maintaining said parallel apposition as said handles are moved between said open and closed positions, and said cartridge housing and U-shaped actuator having at least one pair of crossing slots with a rod extending through each of said pairs of crossing slots and through the lower portion of the channel of said cartridge housing to underlie the staple cartridge when it is positioned in said cartridge housing, to operate said actuator means.

* * * * *